US006444466B1

(12) United States Patent
Ward et al.

(10) Patent No.: US 6,444,466 B1
(45) Date of Patent: Sep. 3, 2002

(54) ANTISENSE MODULATION OF HELICASE-MOI EXPRESSION

(75) Inventors: Donna T. Ward, Murrieta; Andrew T. Watt, Vista, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/853,768

(22) Filed: May 10, 2001

(51) Int. Cl.$^7$ .................... C12Q 1/68; C07H 21/04; C12N 15/85
(52) U.S. Cl. .................... 435/375; 435/6; 435/91.1; 435/325; 435/366; 536/23.1; 536/24.31; 536/24.33; 536/24.5
(58) Field of Search .................... 435/6, 325, 366, 435/375; 536/23.1, 24.5; 514/44

(56) References Cited

PUBLICATIONS

C. Frank Bennett et al., Pharmacology of Antisense Therapeutic Agents, pp. 13–46.*
W. Michael Flanagan et al., Cellular penetration and antisense activity by a phenoxazine–substituted heptanucleotide, Research, pp. 1–5.*
Andrea D. Branch, A good antisense molecular is hard to find. TIBS 23—Feb. 1998, pp. 45–50.*
D.D.F. Ma et al., Synthetic oligonucleotides as therapeutics: the coming of age, Biotechnology Annual Review, vol. 5, pp. 155–196.*
Sudhir Agrawal et al., Antisense therapeutics: is it as simple as compementary base recognition? Molecular Medicine Today, Feb. 2000, vol. 6, pp. 72–81.*
Douglas W. Green et al., Antisense Oligonucleotides: An Evolving Technology for the Modulation of Gene Expression in Human Disease, J. Am. Coll. Surg. pp. 93–105.*
Kuang–Yu Jen, et al., Suppression of Gene Expression by Targeted Disruption of Messenger RNA: Available Options and Current Strategies, Stem Cells, 2000, 18, pp. 307–319.*
Cogoni et al., Posttranscriptional gene silencing in Neurospora by a RecQ DNA helicase, *Science*, 1999, 286:2342–2344.
de la Cruz et al., Unwinding RNA in Saccharomyces cerevisiae: DEAD–box proteins and related families, *Trends Biochem. Sci.*, 1999, 24:192–198.
Matsuda et al., Molecular cloning and characterization of a novel human gene (HERNA) which encodes a putative RNA–helicase, *Biochim. Biophys. Acta*, 2000, 1490:163–169.
Nagase et al., Prediction of the coding sequences of unidentified human genes. XIII. The complete sequences of 100 new cDNA clones from brain which code for large proteins in vitro, *DNA Res.*, 1999, 6:63–70.
Provost et al., Interaction of 5–lipoxygenase with cellular proteins, *Proc. Natl. Acad. Sci. U. S. A.*, 1999, 96:1881–1885.

\* cited by examiner

*Primary Examiner*—John L. LeGuyader
*Assistant Examiner*—Mary M. Schmidt
(74) *Attorney, Agent, or Firm*—Licata & Tyrrell P.C.

(57) ABSTRACT

Antisense compounds, compositions and methods are provided for modulating the expression of helicase-moi. The compositions comprise antisense compounds, particularly antisense oligonucleotides, targeted to nucleic acids encoding helicase-moi. Methods of using these compounds for modulation of helicase-moi expression and for treatment of diseases associated with expression of helicase-moi are provided.

26 Claims, No Drawings

SEQUENCE LISTING

```
<160> NUMBER OF SEQ ID NOS: 91

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                                  20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                                  20

<210> SEQ ID NO 3
<211> LENGTH: 7037
<212> TYPE: DNA
<213> ORGANISM: Homo sapiens
<220> FEATURE:
<221> NAME/KEY: CDS
<222> LOCATION: (183)...(5957)

<400> SEQUENCE: 3
ggaaactctg aaagaactta gaatcagcat tttgagagca gaagcttggg catgctgtga       60
ttttccaata aactgctatc acaatgtcaa aatgcagttc agacaagagc aacacagaga      120
tctcaaacat taaaacgtaa gctgtgctag acaaaaaatg caatgaaaga aacactggat      180 ga atg aaa agc cct gct ttg caa ccc ctc agc atg gca ggc ctg cag        227
   Met Lys Ser Pro Ala Leu Gln Pro Leu Ser Met Ala Gly Leu Gln
    1               5                  10                 15 ctc atg acc cct gct tcc tca cca atg ggt cct ttc ttt gga ctg cca        275
Leu Met Thr Pro Ala Ser Ser Pro Met Gly Pro Phe Phe Gly Leu Pro
             20                  25                  30 tgg caa caa gaa gca att cat gat aac att tat acg cca aga aaa tat        323
Trp Gln Gln Glu Ala Ile His Asp Asn Ile Tyr Thr Pro Arg Lys Tyr
         35                  40                  45 cag gtt gaa ctg ctt gaa gca gct ctg gat cat aat acc atc gtc tgt        371
Gln Val Glu Leu Leu Glu Ala Ala Leu Asp His Asn Thr Ile Val Cys
     50                  55                  60 tta aac act ggc tca ggg aag aca ttt att gct agt act act cta cta        419
Leu Asn Thr Gly Ser Gly Lys Thr Phe Ile Ala Ser Thr Thr Leu Leu
 65                  70                  75 aag agc tgt ctc tat cta gat cta ggg gag act tca gct aga aat gga        467
Lys Ser Cys Leu Tyr Leu Asp Leu Gly Glu Thr Ser Ala Arg Asn Gly
 80                  85                  90                  95 aaa agg acg gtg ttc ttg gtc aac tct gca aac cag gtt gct caa caa        515
Lys Arg Thr Val Phe Leu Val Asn Ser Ala Asn Gln Val Ala Gln Gln
                100                 105                 110
```

-continued

| | |
|---|---|
| gtg tca gct gtc aga act cat tca gat ctc aag gtt ggg gaa tac tca<br>Val Ser Ala Val Arg Thr His Ser Asp Leu Lys Val Gly Glu Tyr Ser<br>115                    120                 125 | 563 |
| aac cta gaa gta aat gca tct tgg aca aaa gag aga tgg aac caa gag<br>Asn Leu Glu Val Asn Ala Ser Trp Thr Lys Glu Arg Trp Asn Gln Glu<br>        130                 135                140 | 611 |
| ttt act aag cac cag gtt ctc att atg act tgc tat gtc gcc ttg aat<br>Phe Thr Lys His Gln Val Leu Ile Met Thr Cys Tyr Val Ala Leu Asn<br>145                    150                 155 | 659 |
| gtt ttg aaa aat ggt tac tta tca ctg tca gac att aac ctt ttg gtg<br>Val Leu Lys Asn Gly Tyr Leu Ser Leu Ser Asp Ile Asn Leu Leu Val<br>160                    165                 170                175 | 707 |
| ttt gat gag tgt cat ctt gca atc cta gac cac ccc tat cga gaa ttt<br>Phe Asp Glu Cys His Leu Ala Ile Leu Asp His Pro Tyr Arg Glu Phe<br>                 180                185                190 | 755 |
| atg aag ctc tgt gaa att tgt cca tca tgt cct cgc att ttg gga cta<br>Met Lys Leu Cys Glu Ile Cys Pro Ser Cys Pro Arg Ile Leu Gly Leu<br>                 195                200                205 | 803 |
| act gct tcc att tta aat ggg aaa tgg gat cca gag gat ttg gaa gaa<br>Thr Ala Ser Ile Leu Asn Gly Lys Trp Asp Pro Glu Asp Leu Glu Glu<br>                 210                215                220 | 851 |
| aag ttt cag aaa cta gag aaa att ctt aag agt aat gct gaa act gca<br>Lys Phe Gln Lys Leu Glu Lys Ile Leu Lys Ser Asn Ala Glu Thr Ala<br>225                    230                 235 | 899 |
| act gac ctg gtg gtc tta gac agg tat act tct cag cca tgt gag att<br>Thr Asp Leu Val Val Leu Asp Arg Tyr Thr Ser Gln Pro Cys Glu Ile<br>240                    245                250                255 | 947 |
| gtg gtg gat tgt gga cca ttt act gac aga agt ggg ctt tat gaa aga<br>Val Val Asp Cys Gly Pro Phe Thr Asp Arg Ser Gly Leu Tyr Glu Arg<br>                 260                265                270 | 995 |
| ctg ctg atg gaa tta gaa gaa gca ctt aat ttt atc aat gat tgt aat<br>Leu Leu Met Glu Leu Glu Glu Ala Leu Asn Phe Ile Asn Asp Cys Asn<br>                 275                280                285 | 1043 |
| ata tct gta cat tca aaa gaa aga gat tct act tta att tcg aaa cag<br>Ile Ser Val His Ser Lys Glu Arg Asp Ser Thr Leu Ile Ser Lys Gln<br>290                    295                300 | 1091 |
| ata cta tca gac tgt cgt gcc gta ttg gta gtt ctg gga ccc tgg tgt<br>Ile Leu Ser Asp Cys Arg Ala Val Leu Val Val Leu Gly Pro Trp Cys<br>                 305                310                315 | 1139 |
| gca gat aaa gta gct gga atg atg gta aga gaa cta cag aaa tac atc<br>Ala Asp Lys Val Ala Gly Met Met Val Arg Glu Leu Gln Lys Tyr Ile<br>320                    325                330                335 | 1187 |
| aaa cat gag caa gag gag ctg cac agg aaa ttt tta ttg ttt aca gac<br>Lys His Glu Gln Glu Glu Leu His Arg Lys Phe Leu Leu Phe Thr Asp<br>                 340                345                350 | 1235 |
| act ttc cta agg aaa ata cat gca cta tgt gaa gag cac ttc tca cct<br>Thr Phe Leu Arg Lys Ile His Ala Leu Cys Glu Glu His Phe Ser Pro<br>                 355                360                365 | 1283 |
| gcc tca ctt gac ctg aaa ttt gta act cct aaa gta atc aaa ctg ctc<br>Ala Ser Leu Asp Leu Lys Phe Val Thr Pro Lys Val Ile Lys Leu Leu<br>370                    375                380 | 1331 |
| gaa atc tta cgc aaa tat aaa cca tat gag cga cac agt ttt gaa agc<br>Glu Ile Leu Arg Lys Tyr Lys Pro Tyr Glu Arg His Ser Phe Glu Ser<br>385                    390                395 | 1379 |
| gtt gag tgg tat aat aat aga aat cag gat aat tat gtg tca tgg agt<br>Val Glu Trp Tyr Asn Asn Arg Asn Gln Asp Asn Tyr Val Ser Trp Ser<br>400                    405                410                415 | 1427 |
| gat tct gag gat gat gat gag gat gaa gaa att gaa gaa aaa gag aag<br>Asp Ser Glu Asp Asp Asp Glu Asp Glu Glu Ile Glu Glu Lys Glu Lys<br>                 420                425                430 | 1475 |

```
cca gag aca aat ttt cct tct cct ttt acc aac att ttg tgc gga att    1523
Pro Glu Thr Asn Phe Pro Ser Pro Phe Thr Asn Ile Leu Cys Gly Ile
            435                 440                 445 att ttt gtg gaa aga aga tac aca gca gtt gtc tta aac aga ttg ata    1571
Ile Phe Val Glu Arg Arg Tyr Thr Ala Val Val Leu Asn Arg Leu Ile
            450                 455                 460 aag gaa gct ggc aaa caa gat cca gag ctg gct tat atc agt agc aat    1619
Lys Glu Ala Gly Lys Gln Asp Pro Glu Leu Ala Tyr Ile Ser Ser Asn
465                 470                 475 ttc ata act gga cat ggc att ggg aag aat cag cct cgc aac aac acg    1667
Phe Ile Thr Gly His Gly Ile Gly Lys Asn Gln Pro Arg Asn Asn Thr
480                 485                 490                 495 atg gaa gca gaa ttc aga aaa cag gaa gag gta ctt agg aaa ttt cga    1715
Met Glu Ala Glu Phe Arg Lys Gln Glu Glu Val Leu Arg Lys Phe Arg
                500                 505                 510 gca cat gag acc aac ctg ctt att gca aca agt att gta gaa gag ggt    1763
Ala His Glu Thr Asn Leu Leu Ile Ala Thr Ser Ile Val Glu Glu Gly
                515                 520                 525 gtt gat ata cca aaa tgc aac ttg gtg gtt cgt ttt gat ttg ccc aca    1811
Val Asp Ile Pro Lys Cys Asn Leu Val Val Arg Phe Asp Leu Pro Thr
            530                 535                 540 gaa tat cga tcc tat gtt caa tct aaa gga aga gca agg gca ccc atc    1859
Glu Tyr Arg Ser Tyr Val Gln Ser Lys Gly Arg Ala Arg Ala Pro Ile
545                 550                 555 tct aat tat ata atg tta gcg gat aca gac aaa ata aaa agt ttt gaa    1907
Ser Asn Tyr Ile Met Leu Ala Asp Thr Asp Lys Ile Lys Ser Phe Glu
560                 565                 570                 575 gaa gac ctt aaa acc tac aaa gct att gaa aag atc ttg aga aac aag    1955
Glu Asp Leu Lys Thr Tyr Lys Ala Ile Glu Lys Ile Leu Arg Asn Lys
                580                 585                 590 tgt tcc aag tcg gtt gat act ggt gag act gac att gat cct gtc atg    2003
Cys Ser Lys Ser Val Asp Thr Gly Glu Thr Asp Ile Asp Pro Val Met
                595                 600                 605 gat gat gat cac gtt ttc cca cca tat gtg ttg agg cct gac gat ggt    2051
Asp Asp Asp His Val Phe Pro Pro Tyr Val Leu Arg Pro Asp Asp Gly
            610                 615                 620 ggt cca cga gtc aca atc aac acg gcc att gga cac atc aat aga tac    2099
Gly Pro Arg Val Thr Ile Asn Thr Ala Ile Gly His Ile Asn Arg Tyr
625                 630                 635 tgt gct aga tta cca agt gat ccg ttt act cat cta gct cct aaa tgc    2147
Cys Ala Arg Leu Pro Ser Asp Pro Phe Thr His Leu Ala Pro Lys Cys
640                 645                 650                 655 aga acc cga gag ttg cct gat ggt aca ttt tat tca act ctt tat ctg    2195
Arg Thr Arg Glu Leu Pro Asp Gly Thr Phe Tyr Ser Thr Leu Tyr Leu
                660                 665                 670 cca att aac tca cct ctt cga gcc tcc att gtt ggt cca cca atg agc    2243
Pro Ile Asn Ser Pro Leu Arg Ala Ser Ile Val Gly Pro Pro Met Ser
                675                 680                 685 tgt gta cga ttg gct gaa aga gtt gtc gct ctc att tgc tgt gag aaa    2291
Cys Val Arg Leu Ala Glu Arg Val Val Ala Leu Ile Cys Cys Glu Lys
            690                 695                 700 ctg cac aaa att ggc gaa ctg gat gac cat ttg atg cca gtt ggg aaa    2339
Leu His Lys Ile Gly Glu Leu Asp Asp His Leu Met Pro Val Gly Lys
705                 710                 715 gag act gtt aaa tat gaa gag gag ctt gat ttg cat gat gaa gaa gag    2387
Glu Thr Val Lys Tyr Glu Glu Glu Leu Asp Leu His Asp Glu Glu Glu
720                 725                 730                 735 acc agt gtt cca gga aga cca ggt tcc acg aaa cga agg cag tgc tac    2435
Thr Ser Val Pro Gly Arg Pro Gly Ser Thr Lys Arg Arg Gln Cys Tyr
```

-continued

|  |  |  |  |
|---|---|---|---|
| | 740 | 745 | 750 |
| cca aaa gca att cca gag tgt ttg agg gat agt tat ccc aga cct gat<br>Pro Lys Ala Ile Pro Glu Cys Leu Arg Asp Ser Tyr Pro Arg Pro Asp<br>                755                    760                765 | | | 2483 |
| cag ccc tgt tac ctg tat gtg ata gga atg gtt tta act aca cct tta<br>Gln Pro Cys Tyr Leu Tyr Val Ile Gly Met Val Leu Thr Thr Pro Leu<br>                770                    775                780 | | | 2531 | cct gat gaa ctc aac ttt aga agg cgg aag ctc tat cct cct gaa gat      2579
Pro Asp Glu Leu Asn Phe Arg Arg Arg Lys Leu Tyr Pro Pro Glu Asp
    785                 790                 795 acc aca aga tgc ttt gga ata ctg acg gcc aaa ccc ata cct cag att      2627
Thr Thr Arg Cys Phe Gly Ile Leu Thr Ala Lys Pro Ile Pro Gln Ile
800                 805                 810                 815 cca cac ttt cct gtg tac aca cgc tct gga gag gtt acc ata tcc att      2675
Pro His Phe Pro Val Tyr Thr Arg Ser Gly Glu Val Thr Ile Ser Ile
                820                 825                 830 gag ttg aag aag tct ggt ttc atg ttg tct cta caa atg ctt gag ttg      2723
Glu Leu Lys Lys Ser Gly Phe Met Leu Ser Leu Gln Met Leu Glu Leu
    835                 840                 845 att aca aga ctt cac cag tat ata ttc tca cat att ctt cgg ctt gaa      2771
Ile Thr Arg Leu His Gln Tyr Ile Phe Ser His Ile Leu Arg Leu Glu
850                 855                 860 aaa cct gca cta gaa ttt aaa cct aca gac gct gat tca gca tac tgt      2819
Lys Pro Ala Leu Glu Phe Lys Pro Thr Asp Ala Asp Ser Ala Tyr Cys
    865                 870                 875 gtt cta cct ctt aat gtt gtt aat gac tcc agc act ttg gat att gac      2867
Val Leu Pro Leu Asn Val Val Asn Asp Ser Ser Thr Leu Asp Ile Asp
880                 885                 890                 895 ttt aaa ttc atg gaa gat att gag aag tct gaa gct cgc ata ggc att      2915
Phe Lys Phe Met Glu Asp Ile Glu Lys Ser Glu Ala Arg Ile Gly Ile
                900                 905                 910 ccc agt aca aag tat aca aaa gaa aca ccc ttt gtt ttt aaa tta gaa      2963
Pro Ser Thr Lys Tyr Thr Lys Glu Thr Pro Phe Val Phe Lys Leu Glu
    915                 920                 925 gat tac caa gat gcc gtt atc att cca aga tat cgc aat ttt gat cag      3011
Asp Tyr Gln Asp Ala Val Ile Ile Pro Arg Tyr Arg Asn Phe Asp Gln
930                 935                 940 cct cat cga ttt tat gta gct gat gtg tac act gat ctt acc cca ctc      3059
Pro His Arg Phe Tyr Val Ala Asp Val Tyr Thr Asp Leu Thr Pro Leu
    945                 950                 955 agt aaa ttt cct tcc cct gag tat gaa act ttt gca gaa tat tat aaa      3107
Ser Lys Phe Pro Ser Pro Glu Tyr Glu Thr Phe Ala Glu Tyr Tyr Lys
960                 965                 970                 975 aca aag tac aac ctt gac cta acc aat ctc aac cag cca ctg ctg gat      3155
Thr Lys Tyr Asn Leu Asp Leu Thr Asn Leu Asn Gln Pro Leu Leu Asp
                980                 985                 990 gtg gac cac aca tct tca aga ctt aat ctt ttg aca cct cga cat ttg      3203
Val Asp His Thr Ser Ser Arg Leu Asn Leu Leu Thr Pro Arg His Leu
    995                 1000                1005 aat cag aag ggg aaa gcg ctt cct tta agc agt gct gag aag agg aaa      3251
Asn Gln Lys Gly Lys Ala Leu Pro Leu Ser Ser Ala Glu Lys Arg Lys
            1010                1015                1020 gcc aaa tgg gaa agt ctg cag aat aaa cag ata ctg gtt cca gaa ctc      3299
Ala Lys Trp Glu Ser Leu Gln Asn Lys Gln Ile Leu Val Pro Glu Leu
1025                1030                1035 tgt gct ata cat cca att cca gca tca ctg tgg aga aaa gct gtt tgt      3347
Cys Ala Ile His Pro Ile Pro Ala Ser Leu Trp Arg Lys Ala Val Cys
1040                1045                1050                1055 ctc ccc agc ata ctt tat cgc ctt cac tgc ctt ttg act gca gag gag      3395

```
                                                         -continued

Leu Pro Ser Ile Leu Tyr Arg Leu His Cys Leu Leu Thr Ala Glu Glu
            1060                1065                1070 cta aga gcc cag act gcc agc gat gct ggc gtg gga gtc aga tca ctt    3443
Leu Arg Ala Gln Thr Ala Ser Asp Ala Gly Val Gly Val Arg Ser Leu
        1075                1080                1085 cct gcg gat ttt aga tac cct aac tta gac ttc ggg tgg aaa aaa tct    3491
Pro Ala Asp Phe Arg Tyr Pro Asn Leu Asp Phe Gly Trp Lys Lys Ser
    1090                1095                1100 att gac agc aaa tct ttc atc tca att tct aac tcc tct tca gct gaa    3539
Ile Asp Ser Lys Ser Phe Ile Ser Ile Ser Asn Ser Ser Ser Ala Glu
        1105                1110                1115 aat gat aat tac tgt aag cac agc aca att gtc cct gaa aat gct gca    3587
Asn Asp Asn Tyr Cys Lys His Ser Thr Ile Val Pro Glu Asn Ala Ala
1120                1125                1130                1135 cat caa ggt gct aat aga acc tcc tct cta gaa aat cat gac caa atg    3635
His Gln Gly Ala Asn Arg Thr Ser Ser Leu Glu Asn His Asp Gln Met
            1140                1145                1150 tct gtg aac tgc aga acg ttg ctc agc gag tcc cct ggt aag ctc cac    3683
Ser Val Asn Cys Arg Thr Leu Leu Ser Glu Ser Pro Gly Lys Leu His
        1155                1160                1165 gtt gaa gtt tca gca gat ctt aca gca att aat ggt ctt tct tac aat    3731
Val Glu Val Ser Ala Asp Leu Thr Ala Ile Asn Gly Leu Ser Tyr Asn
    1170                1175                1180 caa aat ctc gcc aat ggc agt tat gat tta gct aac aga gac ttt tgc    3779
Gln Asn Leu Ala Asn Gly Ser Tyr Asp Leu Ala Asn Arg Asp Phe Cys
        1185                1190                1195 caa gga aat cag cta aat tac tac aag cag gaa ata ccc gtg caa cca    3827
Gln Gly Asn Gln Leu Asn Tyr Tyr Lys Gln Glu Ile Pro Val Gln Pro
1200                1205                1210                1215 act acc tca tat tcc att cag aat tta tac agt tac gag aac cag ccc    3875
Thr Thr Ser Tyr Ser Ile Gln Asn Leu Tyr Ser Tyr Glu Asn Gln Pro
            1220                1225                1230 cag ccc agc gat gaa tgt act ctc ctg agt aat aaa tac ctt gat gga    3923
Gln Pro Ser Asp Glu Cys Thr Leu Leu Ser Asn Lys Tyr Leu Asp Gly
        1235                1240                1245 aat gct aac aaa tct acc tca gat gga agt cct gtg atg gcc gta atg    3971
Asn Ala Asn Lys Ser Thr Ser Asp Gly Ser Pro Val Met Ala Val Met
    1250                1255                1260 cct ggt acg aca gac act att caa gtg ctc aag ggc agg atg gat tct    4019
Pro Gly Thr Thr Asp Thr Ile Gln Val Leu Lys Gly Arg Met Asp Ser
        1265                1270                1275 gag cag agc cct tct att ggg tac tcc tca agg act ctt ggc ccc aat    4067
Glu Gln Ser Pro Ser Ile Gly Tyr Ser Ser Arg Thr Leu Gly Pro Asn
1280                1285                1290                1295 cct gga ctt att ctt cag gct ttg act ctg tca aac gct agt gat gga    4115
Pro Gly Leu Ile Leu Gln Ala Leu Thr Leu Ser Asn Ala Ser Asp Gly
            1300                1305                1310 ttt aac ctg gag cgg ctt gaa atg ctt ggc gac tcc ttt tta aag cat    4163
Phe Asn Leu Glu Arg Leu Glu Met Leu Gly Asp Ser Phe Leu Lys His
        1315                1320                1325 gcc atc acc aca tat cta ttt tgc act tac cct gat gcg cat gag ggc    4211
Ala Ile Thr Thr Tyr Leu Phe Cys Thr Tyr Pro Asp Ala His Glu Gly
    1330                1335                1340 cgc ctt tca tat atg aga agc aaa aag gtc agc aac tgt aat ctg tat    4259
Arg Leu Ser Tyr Met Arg Ser Lys Lys Val Ser Asn Cys Asn Leu Tyr
        1345                1350                1355 cgc ctt gga aaa aag aag gga cta ccc agc cgc atg gtg gtg tca ata    4307
Arg Leu Gly Lys Lys Lys Gly Leu Pro Ser Arg Met Val Val Ser Ile
1360                1365                1370                1375
```

| | |
|---|---|
| ttt gat ccc cct gtg aat tgg ctt cct cct ggt tat gta gta aat caa<br>Phe Asp Pro Pro Val Asn Trp Leu Pro Pro Gly Tyr Val Val Asn Gln<br>              1380                        1385                        1390 | 4355 |
| gac aaa agc aac aca gat aaa tgg gaa aaa gat gaa atg aca aaa gac<br>Asp Lys Ser Asn Thr Asp Lys Trp Glu Lys Asp Glu Met Thr Lys Asp<br>        1395                        1400                        1405 | 4403 |
| tgc atg ctg gcg aat ggc aaa ctg gat gag gat tac gag gag gag gat<br>Cys Met Leu Ala Asn Gly Lys Leu Asp Glu Asp Tyr Glu Glu Glu Asp<br>            1410                        1415                        1420 | 4451 |
| gag gag gag gag agc ctg atg tgg agg gct ccg aag gaa gag gct gac<br>Glu Glu Glu Glu Ser Leu Met Trp Arg Ala Pro Lys Glu Glu Ala Asp<br>        1425                        1430                        1435 | 4499 |
| tat gaa gat gat ttc ctg gag tat gat cag gaa cat atc aga ttt ata<br>Tyr Glu Asp Asp Phe Leu Glu Tyr Asp Gln Glu His Ile Arg Phe Ile<br>1440                        1445                        1450                        1455 | 4547 |
| gat aat atg tta atg ggg tca gga gct ttt gta aag aaa atc tct ctt<br>Asp Asn Met Leu Met Gly Ser Gly Ala Phe Val Lys Lys Ile Ser Leu<br>            1460                        1465                        1470 | 4595 |
| tct cct ttt tca acc act gat tct gca tat gaa tgg aaa atg ccc aaa<br>Ser Pro Phe Ser Thr Thr Asp Ser Ala Tyr Glu Trp Lys Met Pro Lys<br>        1475                        1480                        1485 | 4643 |
| aaa tcc tcc tta ggt agt atg cca ttt tca tca gat ttt gag gat ttt<br>Lys Ser Ser Leu Gly Ser Met Pro Phe Ser Ser Asp Phe Glu Asp Phe<br>            1490                        1495                        1500 | 4691 |
| gac tac agc tct tgg gat gca atg tgc tat ctg gat cct agc aaa gct<br>Asp Tyr Ser Ser Trp Asp Ala Met Cys Tyr Leu Asp Pro Ser Lys Ala<br>        1505                        1510                        1515 | 4739 |
| gtt gaa gaa gat gac ttt gtg gtg ggg ttc tgg aat cca tca gaa gaa<br>Val Glu Glu Asp Asp Phe Val Val Gly Phe Trp Asn Pro Ser Glu Glu<br>1520                        1525                        1530                        1535 | 4787 |
| aac tgt ggt gtt gac acg gga aag cag tcc att tct tac gac ttg cac<br>Asn Cys Gly Val Asp Thr Gly Lys Gln Ser Ile Ser Tyr Asp Leu His<br>            1540                        1545                        1550 | 4835 |
| act gag cag tgt att gct gac aaa agc ata gcg gac tgt gtg gaa gcc<br>Thr Glu Gln Cys Ile Ala Asp Lys Ser Ile Ala Asp Cys Val Glu Ala<br>        1555                        1560                        1565 | 4883 |
| ctg ctg ggc tgc tat tta acc agc tgt ggg gag agg gct gct cag ctt<br>Leu Leu Gly Cys Tyr Leu Thr Ser Cys Gly Glu Arg Ala Ala Gln Leu<br>            1570                        1575                        1580 | 4931 |
| ttc ctc tgt tca ctg ggg ctg aag gtg ctc ccg gta att aaa agg act<br>Phe Leu Cys Ser Leu Gly Leu Lys Val Leu Pro Val Ile Lys Arg Thr<br>        1585                        1590                        1595 | 4979 |
| gat cgg gaa aag gcc ctg tgc cct act cgg gag aat ttc aac agc caa<br>Asp Arg Glu Lys Ala Leu Cys Pro Thr Arg Glu Asn Phe Asn Ser Gln<br>1600                        1605                        1610                        1615 | 5027 |
| caa aag aac ctt tca gtg agc tgt gct gct gct tct gtg gcc agt tca<br>Gln Lys Asn Leu Ser Val Ser Cys Ala Ala Ala Ser Val Ala Ser Ser<br>            1620                        1625                        1630 | 5075 |
| cgc tct tct gta ttg aaa gac tcg gaa tat ggt tgt ttg aag att cca<br>Arg Ser Ser Val Leu Lys Asp Ser Glu Tyr Gly Cys Leu Lys Ile Pro<br>        1635                        1640                        1645 | 5123 |
| cca aga tgt atg ttt gat cat cca gat gca gat aaa aca ctg aat cac<br>Pro Arg Cys Met Phe Asp His Pro Asp Ala Asp Lys Thr Leu Asn His<br>            1650                        1655                        1660 | 5171 |
| ctt ata tcg ggg ttt gaa aat ttt gaa aag aaa atc aac tac aga ttc<br>Leu Ile Ser Gly Phe Glu Asn Phe Glu Lys Lys Ile Asn Tyr Arg Phe<br>        1665                        1670                        1675 | 5219 |
| aag aat aag gct tac ctt ctc cag gct ttt aca cat gcc tcc tac cac<br>Lys Asn Lys Ala Tyr Leu Leu Gln Ala Phe Thr His Ala Ser Tyr His<br>1680                        1685                        1690                        1695 | 5267 |

-continued

| | | |
|---|---|---|
| tac aat act atc act gat tgt tac cag cgc tta gaa ttc ctg gga gat<br>Tyr Asn Thr Ile Thr Asp Cys Tyr Gln Arg Leu Glu Phe Leu Gly Asp<br>                  1700                            1705                      1710 | 5315 |
| gcg att ttg gac tac ctc ata acc aag cac ctt tat gaa gac ccg cgg<br>Ala Ile Leu Asp Tyr Leu Ile Thr Lys His Leu Tyr Glu Asp Pro Arg<br>                  1715                          1720                      1725 | 5363 |
| cag cac tcc ccg ggg gtc ctg aca gac ctg cgg tct gcc ctg gtc aac<br>Gln His Ser Pro Gly Val Leu Thr Asp Leu Arg Ser Ala Leu Val Asn<br>        1730                          1735                      1740 | 5411 |
| aac acc atc ttt gca tcg ctg gct gta aag tac gac tac cac aag tac<br>Asn Thr Ile Phe Ala Ser Leu Ala Val Lys Tyr Asp Tyr His Lys Tyr<br>        1745                          1750                      1755 | 5459 |
| ttc aaa gct gtc tct cct gag ctc ttc cat gtc att gat gac ttt gtg<br>Phe Lys Ala Val Ser Pro Glu Leu Phe His Val Ile Asp Asp Phe Val<br>1760                          1765                      1770                      1775 | 5507 |
| cag ttt cag ctt gag aag aat gaa atg caa gga atg gat tct gag ctt<br>Gln Phe Gln Leu Glu Lys Asn Glu Met Gln Gly Met Asp Ser Glu Leu<br>                  1780                          1785                      1790 | 5555 |
| agg aga tct gag gag gat gaa gag aaa gaa gag gat att gaa gtt cca<br>Arg Arg Ser Glu Glu Asp Glu Glu Lys Glu Glu Asp Ile Glu Val Pro<br>        1795                          1800                      1805 | 5603 |
| aag gcc atg ggg gat att ttt gag tcg ctt gct ggt gcc att tac atg<br>Lys Ala Met Gly Asp Ile Phe Glu Ser Leu Ala Gly Ala Ile Tyr Met<br>            1810                        1815                      1820 | 5651 |
| gat agt ggg atg tca ctg gag aca gtc tgg cag gtg tac tat ccc atg<br>Asp Ser Gly Met Ser Leu Glu Thr Val Trp Gln Val Tyr Tyr Pro Met<br>        1825                          1830                      1835 | 5699 |
| atg cgg cca cta ata gaa aag ttt tct gca aat gta ccc cgt tcc cct<br>Met Arg Pro Leu Ile Glu Lys Phe Ser Ala Asn Val Pro Arg Ser Pro<br>1840                        1845                      1850                      1855 | 5747 |
| gtg cga gaa ttg ctt gaa atg gaa cca gaa act gcc aaa ttt agc ccg<br>Val Arg Glu Leu Leu Glu Met Glu Pro Glu Thr Ala Lys Phe Ser Pro<br>                  1860                          1865                      1870 | 5795 |
| gct gag aga act tac gac ggg aag gtc aga gtc act gtg gaa gta gta<br>Ala Glu Arg Thr Tyr Asp Gly Lys Val Arg Val Thr Val Glu Val Val<br>        1875                          1880                      1885 | 5843 |
| gga aag ggg aaa ttt aaa ggt gtt ggt cga agt tac agg att gcc aaa<br>Gly Lys Gly Lys Phe Lys Gly Val Gly Arg Ser Tyr Arg Ile Ala Lys<br>        1890                          1895                      1900 | 5891 |
| tct gca gca gca aga aga gcc ctc cga agc ctc aaa gct aat caa cct<br>Ser Ala Ala Ala Arg Arg Ala Leu Arg Ser Leu Lys Ala Asn Gln Pro<br>        1905                          1910                      1915 | 5939 |
| cag gtt ccc aat agc tga aaccgctttt taaaattcaa aacaagaaac<br>Gln Val Pro Asn Ser *<br>1920 | 5987 |
| aaaacaaaaa aaattaaggg gaaaattatt taaatcggaa aggaagactt aaagttgata | 6047 |
| gtgagtggaa tgaattgaag gcagaattta agtttggtt gataacagga tagataacag | 6107 |
| aataaaacat ttaacatatg tataaaattt tggaactaat tgtagtttta gttttttgcg | 6167 |
| caaacacaat cttatcttct ttcctcactt ctgctttgtt taaatcacaa gagtgcttta | 6227 |
| atgatgacat ttagcaagtg ctcaaaataa ttgacaggtt ttgtttttt tttttgagt | 6287 |
| ttatgtcagc tttgcttagt gttagaaggc catggagctt aaacctccag cagtccctag | 6347 |
| gatgatgtag attcttctcc atctctccgt gtgtgcagta gtgccagtcc tgcagtagtt | 6407 |
| gataagctga atagaaagat aaggttttcg agaggagaag tgcgccaatg ttgtcttttc | 6467 |
| tttccacgtt atactgtgta aggtgatgtt cccggtcgct gttgcacctg atagtaaggg | 6527 |

-continued

```
acagattttt aatgaacatt ggctggcatg ttggtgaatc acattttagt tttctgatgc    6587
cacatagtct tgcataaaaa agggttcttg ccttaaaagt gaaaccttca tggatagtct    6647
ttaatctctg atcttttttgg aacaaactgt tttacattcc tttcatttta ttatgcatta   6707
```
(Note: corrected line below)
```
ttaatctctg atctttttgg aacaaactgt tttacattcc tttcatttta ttatgcatta    6707
gacgttgaga cagcgtgata cttacaactc actagtatag ttgtaactta ttacaggatc    6767
atactaaaat ttctgtcata tgtatactga agacatttta aaaaccagaa tatgtagtct    6827
acggatattt tttatcataa aaatgatctt tggctaaaca ccccatttta ctaaagtcct    6887
cctgccaggt agttcccact gatggaaatg tttatggcaa ataattttgc cttctaggct    6947
gttgctctaa caaataaac cttagacata tcacacctaa aatatgctgc agattttata    7007
attgattggt tacttattta agaagcaaaa                                     7037

<210> SEQ ID NO 4
<211> LENGTH: 22
<212> TYPE: DNA
<213> ORGANISM: Artificial Sequence
<220> FEATURE:
<223> OTHER INFORMATION: PCR Primer

<400> SEQUENCE: 4
ttaaagcatg ccatcaccac at                                               22

<210> SEQ ID NO 5
<211> LENGTH: 24
<212> TYPE: DNA
<213> ORGANISM: Artificial Sequence
<220> FEATURE:
<223> OTHER INFORMATION: PCR Primer

<400> SEQUENCE: 5
gattacagtt gctgaccttt ttgc                                             24

<210> SEQ ID NO 6
<211> LENGTH: 18
<212> TYPE: DNA
<213> ORGANISM: Artificial Sequence
<220> FEATURE:
<223> OTHER INFORMATION: PCR Probe

<400> SEQUENCE: 6
atgcgcatga gggccgcc                                                    18

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                   19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                  20
```

```
<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                      20

<210> SEQ ID NO 10
<211> LENGTH: 5852
<212> TYPE: DNA
<213> ORGANISM: Homo sapiens
<220> FEATURE:
<221> NAME/KEY: CDS
<222> LOCATION: (1)...(4568)

<400> SEQUENCE: 10 ata ata ata gaa atc agg ata att atg tgt cat gga gtg att ctg agg         48
Ile Ile Ile Glu Ile Arg Ile Ile Met Cys His Gly Val Ile Leu Arg
 1               5                  10                  15 atg atg atg agg atg aag aaa ttg aag aaa aag aga agc cag aga caa         96
Met Met Met Arg Met Lys Lys Leu Lys Lys Lys Arg Ser Gln Arg Gln
             20                  25                  30 att ttc ctt ctc ctt tta cca aca ttt tgt gcg gaa tta ttt ttg tgg        144
Ile Phe Leu Leu Leu Leu Pro Thr Phe Cys Ala Glu Leu Phe Leu Trp
         35                  40                  45 aaa gaa gat aca cag cag ttg tct taa aca gat tga taa agg aag ctg        192
Lys Glu Asp Thr Gln Gln Leu Ser  *  Thr Asp  *   *  Arg Lys Leu
 50                  55                                  60 gca aac aag atc cag agc tgg ctt ata tca gta gca att tca taa ctg        240
Ala Asn Lys Ile Gln Ser Trp Leu Ile Ser Val Ala Ile Ser  *  Leu
             65                  70                  75 gac atg gca ttg gga aga atc agc ctc gca aca aac aga tgg aag cag        288
Asp Met Ala Leu Gly Arg Ile Ser Leu Ala Thr Asn Arg Trp Lys Gln
         80                  85                  90 aat tca gaa aac agg aag agg tac tta gga aat ttc gag cac atg aga        336
Asn Ser Glu Asn Arg Lys Arg Tyr Leu Gly Asn Phe Glu His Met Arg
     95                 100                 105 cca acc tgc tta ttg caa caa gta ttg tag aag agg gtg ttg ata tac        384
Pro Thr Cys Leu Leu Gln Gln Val Leu  *  Lys Arg Val Leu Ile Tyr
110                 115                 120 caa aat gca act tgg tgg ttc gtt ttg att tgc cca cag aat atc gat        432
Gln Asn Ala Thr Trp Trp Phe Val Leu Ile Cys Pro Gln Asn Ile Asp
    125                 130                 135 cct atg ttc aat cta aag gaa gag caa ggg cac cca tct cta att ata        480
Pro Met Phe Asn Leu Lys Glu Glu Gln Gly His Pro Ser Leu Ile Ile
140                 145                 150                 155 taa tgt tag cgg ata cag aca aaa taa aaa gtt tga aag aag acc tta        528
 *  Cys  *  Arg Ile Gln Thr Lys  *  Lys Val Leu Lys Lys Thr Leu
                    160                 165 aaa cct aca aag cta ttg aaa aga tct tga gaa aca agt gtt cca agt        576
Lys Pro Thr Lys Leu Leu Lys Arg Ser  *  Glu Thr Ser Val Pro Ser
    170                 175                 180 cgg ttg ata ctg gtg aga ctg aca ttg atc ctg tca tgg atg atg atg        624
Arg Leu Ile Leu Val Arg Leu Thr Leu Ile Leu Ser Trp Met Met Met
185                 190                 195 acg ttt tcc cac cat atg tgt tga ggc ctg acg atg gtg gtc cac gag        672
Thr Phe Ser His His Met Cys  *  Gly Leu Thr Met Val Val His Glu
200                 205                 210 tca caa tca aca cgg cca ttg gac aca tca ata gat act gtg cta gat        720
```

```
Ser Gln Ser Thr Arg Pro Leu Asp Thr Ser Ile Asp Thr Val Leu Asp
215                 220                 225                 230 tac caa gtg atc cgt tta ctc atc tag ctc cta aat gca gaa ccc gag      768
Tyr Gln Val Ile Arg Leu Leu Ile  *  Leu Leu Asn Ala Glu Pro Glu
                    235                 240                 245 agt tgc ctg atg gta cat ttt att caa ctc ttt atc tgc caa tta act      816
Ser Cys Leu Met Val His Phe Ile Gln Leu Phe Ile Cys Gln Leu Thr
                250                 255                 260 cac ctc ttc gag cct cca ttg ttg gtc cac caa tga gct gtg tac gat      864
His Leu Phe Glu Pro Pro Leu Leu Val His Gln  *  Ala Val Tyr Asp
                265                 270                 275 tgg ctg aaa gag ttg tag ctc tca ttt gct gtg aga aac tgc aca aaa      912
Trp Leu Lys Glu Leu  *  Leu Ser Phe Ala Val Arg Asn Cys Thr Lys
                280                 285                 290 ttg gcg aac tgg atg acc att tga tgc cag ttg gga aag aga ctg tta      960
Leu Ala Asn Trp Met Thr Ile  *  Cys Gln Leu Gly Lys Arg Leu Leu
                295                 300                 305 aat atg aag agg agc ttg att tgc atg atg aag aag aga cca gtg ttc     1008
Asn Met Lys Arg Ser Leu Ile Cys Met Met Lys Lys Arg Pro Val Phe
                310                 315                 320 cag gaa gac cag gtt cca cga aac gaa ggc agt gct acc caa aag caa     1056
Gln Glu Asp Gln Val Pro Arg Asn Glu Gly Ser Ala Thr Gln Lys Gln
                325                 330                 335 ttc cag agt gtt tga ggg ata gtt atc cca gac ctg atc agc cct gtt     1104
Phe Gln Ser Val  *  Gly Ile Val Ile Pro Asp Leu Ile Ser Pro Val
                340                 345                 350 acc tgt atg tga tag gaa tgg ttt taa cta cac ctt tac ctg atg aac     1152
Thr Cys Met  *   *  Glu Trp Phe  *  Leu His Leu Tyr Leu Met Asn
                355                 360                 365 tca act tta gaa ggc gga agc tct atc ctc ctg aag ata cca caa gat     1200
Ser Thr Leu Glu Gly Gly Ser Ser Ile Leu Leu Lys Ile Pro Gln Asp
                370                 375                 380 gct ttg gaa tac tga cgg cca aac cca tac ctc aga ttc cac act ttc     1248
Ala Leu Glu Tyr  *  Arg Pro Asn Pro Tyr Leu Arg Phe His Thr Phe
                385                 390                 395 ctg tgt aca cac gct ctg gag agg tta cca tat cca ttg agt tga aga     1296
Leu Cys Thr His Ala Leu Glu Arg Leu Pro Tyr Pro Leu Ser  *  Arg
                400                 405                 410 agt ctg gtt tca tgt tgt ctc tac aaa tgc ttg agt tga tta caa gac     1344
Ser Leu Val Ser Cys Cys Leu Tyr Lys Cys Leu Ser  *  Leu Gln Asp
                415                 420                 425 ttc acc agt ata tat tct cac ata ttc ttc ggc ttg aaa aac ctg cac     1392
Phe Thr Ser Ile Tyr Ser His Ile Phe Phe Gly Leu Lys Asn Leu His
                430                 435                 440 tag aat tta aac cta cag acg ctg att cag cat act gtg ttc tac ctc     1440
 *  Asn Leu Asn Leu Gln Thr Leu Ile Gln His Thr Val Phe Tyr Leu
                445                 450                 455 tta atg ttg tta atg act cca gca ctt tgg ata ttg act tta aat tca     1488
Leu Met Leu Leu Met Thr Pro Ala Leu Trp Ile Leu Thr Leu Asn Ser
                460                 465                 470 tgg aag ata ttg aga agt ctg aag ctc gca tag gca ttc cca gta caa     1536
Trp Lys Ile Leu Arg Ser Leu Lys Leu Ala  *  Ala Phe Pro Val Gln
475                 480                 485 agt ata caa aag aaa cac cct ttg ttt tta aat tag aag att acc aag     1584
Ser Ile Gln Lys Lys His Pro Leu Phe Leu Asn  *  Lys Ile Thr Lys
490                 495                 500 atg ccg tta tca ttc caa gat atc gca att ttg atc agc ctc atc gat     1632
Met Pro Leu Ser Phe Gln Asp Ile Ala Ile Leu Ile Ser Leu Ile Asp
505                 510                 515                 520
```

```
ttt atg tag ctg atg tgt aca ctg atc tta ccc cac tca gta aat ttc    1680
Phe Met  *  Leu Met Cys Thr Leu Ile Leu Pro His Ser Val Asn Phe
             525                 530                 535 ctt ccc ctg agt atg aaa ctt ttg cag aat att ata aaa caa agt aca    1728
Leu Pro Leu Ser Met Lys Leu Leu Gln Asn Ile Ile Lys Gln Ser Thr
             540                 545                 550 acc ttg acc taa cca atc tca acc agc cac tgc tgg atg tgg acc aca    1776
Thr Leu Thr  *  Pro Ile Ser Thr Ser His Cys Trp Met Trp Thr Thr
             555                 560                 565 cat ctt caa gac tta atc ttt tga cac ctc gac att tga atc aga agg    1824
His Leu Gln Asp Leu Ile Phe  *  His Leu Asp Ile  *  Ile Arg Arg
             570                 575                 580 gga aag cgc ttc ctt taa gca gtg ctg aga aga gga aag cca aat ggg    1872
Gly Lys Arg Phe Leu  *  Ala Val Leu Arg Arg Gly Lys Pro Asn Gly
             585                 590                 595 aaa gtc tgc aga ata aac aga tac tgg ttc cag aac tct gtg cta tac    1920
Lys Val Cys Arg Ile Asn Arg Tyr Trp Phe Gln Asn Ser Val Leu Tyr
             600                 605                 610 atc caa ttc cag cat cac tgt gga gaa aag ctg ttt gtc tcc cca gca    1968
Ile Gln Phe Gln His His Cys Gly Glu Lys Leu Phe Val Ser Pro Ala
             615                 620                 625 tac ttt atc gcc ttc act gcc ttt tga ctg cag agg agc taa gag ccc    2016
Tyr Phe Ile Ala Phe Thr Ala Phe  *  Leu Gln Arg Ser  *  Glu Pro
             630                 635                 640 aga ctg cca gcg atg ctg gcg tgg gag tca gat cac ttc ctg cgg att    2064
Arg Leu Pro Ala Met Leu Ala Trp Glu Ser Asp His Phe Leu Arg Ile
             645                 650                 655 tta gat acc cta act tag act tcg ggt gga aaa aat cta ttg aca gca    2112
Leu Asp Thr Leu Thr  *  Thr Ser Gly Gly Lys Asn Leu Leu Thr Ala
             660                 665                 670 aat ctt tca tct caa ttt cta act cct ctt cag ctg aaa atg ata att    2160
Asn Leu Ser Ser Gln Phe Leu Thr Pro Leu Gln Leu Lys Met Ile Ile
             675                 680                 685 act gta agc aca gca caa ttg tcc ctg aaa atg ctg cac atc aag gtg    2208
Thr Val Ser Thr Ala Gln Leu Ser Leu Lys Met Leu His Ile Lys Val
             690                 695                 700 cta ata gaa cct cct ctc tag aaa atc atg acc aaa tgt ctg tga act    2256
Leu Ile Glu Pro Pro Leu  *  Lys Ile Met Thr Lys Cys Leu  *  Thr
705                  710                 715 gca gaa cgt tgc tca gcg agt ccc ctg gta agc tcc acg ttg aag ttt    2304
Ala Glu Arg Cys Ser Ala Ser Pro Leu Val Ser Ser Thr Leu Lys Phe
720                  725                 730 cag cag atc tta cag caa tta atg gtc ttt ctt aca atc aaa atc tcg    2352
Gln Gln Ile Leu Gln Gln Leu Met Val Phe Leu Thr Ile Lys Ile Ser
735                  740                 745                 750 cca atg gca gtt atg att tag cta aca gag act ttt gcc aag gaa atc    2400
Pro Met Ala Val Met Ile  *  Leu Thr Glu Thr Phe Ala Lys Glu Ile
             755                 760                 765 agc taa att act aca agc agg aaa tac ccg tgc aac caa cta cct cat    2448
Ser  *  Ile Thr Thr Ser Arg Lys Tyr Pro Cys Asn Gln Leu Pro His
             770                 775                 780 att cca ttc aga att tat aca gtt acg aga acc agc ccc agc cca gcg    2496
Ile Pro Phe Arg Ile Tyr Thr Val Thr Arg Thr Ser Pro Ser Pro Ala
             785                 790                 795 atg aat gta ctc tcc tga gta ata aat acc ttg atg gaa atg cta aca    2544
Met Asn Val Leu Ser  *  Val Ile Asn Thr Leu Met Glu Met Leu Thr
             800                 805                 810 aat cta cct cag atg gaa gtc ctg tga tgg ccg taa tgc ctg gta cga    2592
Asn Leu Pro Gln Met Glu Val Leu  *  Trp Pro  *  Cys Leu Val Arg
             815                 820                 825
```

-continued

```
cag aca cta ttc aag tgc tca agg gca gga tgg att ctg agc aga gcc    2640
Gln Thr Leu Phe Lys Cys Ser Arg Ala Gly Trp Ile Leu Ser Arg Ala
            830                 835                 840 ctt cta ttg ggt act cct caa gga ctc ttg gcc cca atc ctg gac tta    2688
Leu Leu Leu Gly Thr Pro Gln Gly Leu Leu Ala Pro Ile Leu Asp Leu
        845                 850                 855 ttc ttc agg ctt tga ctc tgt caa acg cta gtg atg gat tta acc tgg    2736
Phe Phe Arg Leu  *  Leu Cys Gln Thr Leu Val Met Asp Leu Thr Trp
    860                 865                 870 agc ggc ttg aaa tgc ttg gcg act cct ttt taa agc atg cca tca cca    2784
Ser Gly Leu Lys Cys Leu Ala Thr Pro Phe  *  Ser Met Pro Ser Pro
875                 880                 885 cat atc tat ttt gca ctt acc ctg atg cgc atg agg gcc gcc ttt cat    2832
His Ile Tyr Phe Ala Leu Thr Leu Met Arg Met Arg Ala Ala Phe His
        890                 895                 900 ata tga gaa gca aaa agg tca gca act gta atc tgt atc gcc ttg gaa    2880
Ile  *  Glu Ala Lys Arg Ser Ala Thr Val Ile Cys Ile Ala Leu Glu
    905                 910                 915 aaa aga agg gac tac cca gcc gca tgg tgg tgt caa tat ttg atc ccc    2928
Lys Arg Arg Asp Tyr Pro Ala Ala Trp Trp Cys Gln Tyr Leu Ile Pro
920                 925                 930 ctg tga att ggc ttc ctc ctg gtt atg tag taa atc aag aca aaa gca    2976
Leu  *  Ile Gly Phe Leu Leu Val Met  *   *  Ile Lys Thr Lys Ala
935                 940                         945 aca cag ata aat ggg aaa aag atg aaa tga caa aag act gca tgc tgg    3024
Thr Gln Ile Asn Gly Lys Lys Met Lys  *  Gln Lys Thr Ala Cys Trp
        950                 955                 960 cga atg gca aac tgg atg agg att acg agg agg agg atg agg agg agg    3072
Arg Met Ala Asn Trp Met Arg Ile Thr Arg Arg Arg Met Arg Arg Arg
    965                 970                 975 aga gcc tga tgt gga ggg ctc cga agg aag agg ctg act atg aag atg    3120
Arg Ala  *  Cys Gly Gly Leu Arg Arg Lys Arg Leu Thr Met Lys Met
980                 985                 990 att tcc tgg agt atg atc agg aac ata tca gat tta tag ata ata tgt    3168
Ile Ser Trp Ser Met Ile Arg Asn Ile Ser Asp Leu  *  Ile Ile Cys
        995                 1000                1005 taa tgg ggt cag gag ctt ttg taa aga aaa tct ctc ttt ctc ctt ttt    3216
 *  Trp Gly Gln Glu Leu Leu  *  Arg Lys Ser Leu Phe Leu Leu Phe
        1010                1015                1020 caa cca ctg att ctg cat atg aat gga aaa tgc cca aaa aat cct cct    3264
Gln Pro Leu Ile Leu His Met Asn Gly Lys Cys Pro Lys Asn Pro Pro
    1025                1030                1035 tag gta gta tgc cat ttt cat cag att ttg agg att ttg act aca gct    3312
 *  Val Val Cys His Phe His Gln Ile Leu Arg Ile Leu Thr Thr Ala
    1040                1045                1050 ctt ggg atg caa tgt gct atc tgg atc cta gca aag ctg ttg aag aag    3360
Leu Gly Met Gln Cys Ala Ile Trp Ile Leu Ala Lys Leu Leu Lys Lys
    1055                1060                1065 atg act ttg tgg tgg ggt tct gga atc cat cag aag aaa act gtg gtg    3408
Met Thr Leu Trp Trp Gly Ser Gly Ile His Gln Lys Lys Thr Val Val
1070                1075                1080                1085 ttg aca cgg gaa agc agt cca ttt ctt acg act tgc aca ctg agc agt    3456
Leu Thr Arg Glu Ser Ser Pro Phe Leu Thr Thr Cys Thr Leu Ser Ser
            1090                1095                1100 gta ttg ctg aca aaa gca tag cgg act gtg tgg aag ccc tgc tgg gct    3504
Val Leu Leu Thr Lys Ala  *  Arg Thr Val Trp Lys Pro Cys Trp Ala
        1105                1110                1115 gct att aac cca gct gtg ggg aga ggg ctg ctc agc ttt tcc tct gtt    3552
Ala Ile  *  Pro Ala Val Gly Arg Gly Leu Leu Ser Phe Ser Ser Val
```

|   |   |   |
|---|---|---|
| cac tgg ggc tga agg tgc tcc cgg taa tta aaa gga ctg atc ggg aaa | 3600 |
| His Trp Gly * Arg Cys Ser Arg * Leu Lys Gly Leu Ile Gly Lys | |
|     1135             1140            1145 | |
| agg ccc tgt gcc cta ctc ggg aga att tca aca gcc aac aaa aga acc | 3648 |
| Arg Pro Cys Ala Leu Leu Gly Arg Ile Ser Thr Ala Asn Lys Arg Thr | |
| 1150             1155             1160 | |
| ttt cag tga gct gtg ctg ctg ctt ctg tgg cca gtt cac gct ctt ctg | 3696 |
| Phe Gln * Ala Val Leu Leu Leu Leu Trp Pro Val His Ala Leu Leu | |
|     1165             1170             1175 | |
| tat tga aag act cgg aat atg gtt gtt tga aga ttc cac caa gat gta | 3744 |
| Tyr * Lys Thr Arg Asn Met Val Val * Arg Phe His Gln Asp Val | |
|     1180             1185             1190 | |
| tgt ttg atc atc cag atg cag ata aaa cac tga atc acc tta tat cgg | 3792 |
| Cys Leu Ile Ile Gln Met Gln Ile Lys His * Ile Thr Leu Tyr Arg | |
|     1195             1200             1205 | |
| ggt ttg aaa att ttg aaa aga aaa tca act aca gat tca aga ata agg | 3840 |
| Gly Leu Lys Ile Leu Lys Arg Lys Ser Thr Thr Asp Ser Arg Ile Arg | |
|     1210             1215             1220 | |
| ctt acc ttc tcc agg ctt tta cac atg cct cct acc act aca ata cta | 3888 |
| Leu Thr Phe Ser Arg Leu Leu His Met Pro Pro Thr Thr Thr Ile Leu | |
|     1225             1230             1235 | |
| tca ctg att gtt acc agc gct tag aat tcc tgg gag atg cga ttt tgg | 3936 |
| Ser Leu Ile Val Thr Ser Ala * Asn Ser Trp Glu Met Arg Phe Trp | |
|     1240             1245             1250 | |
| act acc tca taa cca agc acc ttt atg aag acc cgc ggc agc act ccc | 3984 |
| Thr Thr Ser * Pro Ser Thr Phe Met Lys Thr Arg Gly Ser Thr Pro | |
|     1255             1260             1265 | |
| cgg ggg tcc tga cag acc tgc ggt ctg ccc tgg tca aca aca cca tct | 4032 |
| Arg Gly Ser * Gln Thr Cys Gly Leu Pro Trp Ser Thr Thr Pro Ser | |
|     1270             1275             1280 | |
| ttg cat cgc tgg ctg taa agt acg act acc aca agt act tca aag ctg | 4080 |
| Leu His Arg Trp Leu * Ser Thr Thr Thr Ser Thr Ser Lys Leu | |
|     1285             1290             1295 | |
| tct ctc ctg agc tct tcc atg tca ttg atg act ttg tgc agt ttc agc | 4128 |
| Ser Leu Leu Ser Ser Ser Met Ser Leu Met Thr Leu Cys Ser Phe Ser | |
|     1300             1305             1310 | |
| ttg aga aga atg aaa tgc aag gaa tgg att ctg agc tta gga gat ctg | 4176 |
| Leu Arg Arg Met Lys Cys Lys Glu Trp Ile Leu Ser Leu Gly Asp Leu | |
|     1315             1320             1325 | |
| agg agg atg aag aga aag aag agg ata ttg aag ttc caa agg cca tgg | 4224 |
| Arg Arg Met Lys Arg Lys Lys Arg Ile Leu Lys Phe Gln Arg Pro Trp | |
| 1330             1335             1340             1345 | |
| ggg ata ttt ttg agt cgc ttg ctg gtg cca ttt aca tgg ata gtg gga | 4272 |
| Gly Ile Phe Leu Ser Arg Leu Leu Val Pro Phe Thr Trp Ile Val Gly | |
|         1350             1355             1360 | |
| tgt cac tgg aga cag tct ggc agg tgt act atc cca tga tgc ggc cac | 4320 |
| Cys His Trp Arg Gln Ser Gly Arg Cys Thr Ile Pro * Cys Gly His | |
|     1365             1370             1375 | |
| taa tag aaa agt ttt ctg caa atg tac ccc gtt ccc ctg tgc gag aat | 4368 |
| * * Lys Ser Phe Leu Gln Met Tyr Pro Val Pro Leu Cys Glu Asn | |
|         1380             1385             1390 | |
| tgc ttg aaa tgg aac cag aaa ctg cca aat tta gcc cgg ctg aga gaa | 4416 |
| Cys Leu Lys Trp Asn Gln Lys Leu Pro Asn Leu Ala Arg Leu Arg Glu | |
|     1395             1400             1405 | |
| ctt acg acg gga agg tca gag tca ctg tgg aag tag tag gaa agg gga | 4464 |
| Leu Thr Thr Gly Arg Ser Glu Ser Leu Trp Lys * * Glu Arg Gly | |
|     1410             1415             1420 | |
| aat tta aag gtg ttg gtc gaa gtt aca gga ttg cca aat ctg cag cag | 4512 |

```
Asn Leu Lys Val Leu Val Glu Val Thr Gly Leu Pro Asn Leu Gln Gln
            1425                1430                1435 caa gaa gag ccc tcc gaa gcc tca aag cta atc aac ctc agg ttc cca       4560
Gln Glu Glu Pro Ser Glu Ala Ser Lys Leu Ile Asn Leu Arg Phe Pro
        1440                1445                1450 ata gct ga aaccgctttt taaaattcaa acaagaaac aaaacaaaaa aaattaaggg      4618
Ile Ala gaaaattatt taaatcggaa aggaagactt aaagttgata gtgagtggaa tgaattgaag     4678
gcagaattta aagtttggtt gataacagga tagataacag aataaaacat ttaacatatg     4738
tataaaattt tggaactaat tgtagtttta gtttttttgcg caaacacaat cttatcttct    4798
ttcctcactt ctgctttgtt taaatcacaa gagtgcttta atgatgacat ttagcaagtg     4858
ctcaaaataa ttgacaggtt ttgtttttttt tttttttgagt ttatgtcagc tttgcttagt   4918
gttagaaggc catggagctt aaacctccag cagtccctag gatgatgtag attcttctcc     4978
atctctccgt gtgtgcagta gtgccagtcc tgcagtagtt gataagctga atagaaagat     5038
aaggttttcg agaggagaag tgcgccaatg ttgtcttttc tttccacgtt atactgtgta     5098
aggtgatgtt cccggtcgct gttgcacctg atagtaaggg acagattttt aatgaacatt     5158
ggctggcatg ttggtgaatc acattttagt tttctgatgc cacatagtct tgcataaaaa     5218
agggttcttg ccttaaaagt gaaaccttca tggatagtct ttaatctctg atcttttttgg   5278 aacaaactgt tttacattcc tttcatttta ttatgcatta gacgttgaga cagcgtgata    5338
cttacaactc actagtatag ttgtaactta ttacaggatc atactaaaat ttctgtcata    5398
tgtatactga agacatttta aaaccagaa tatgtagtct acggatattt tttatcataa    5458
aaatgatctt tggctaaaca ccccatttta ctaaagtcct cctgccaggt agttcccact    5518
gatggaaatg tttatggcaa ataattttgc cttctaggct gttgctctaa caaaataaac    5578
cttagacata tcacacctaa aatatgctgc agatttata attgattggt tacttattta    5638
agaagcaaaa cacagcacct ttaccttag tctcctcaca taaatttctt actatacttt    5698
tcataatgtt gcatgcatat ttcacctacc aaagctgtgc tgttaatgcc gtgaaagttt    5758
aacgtttgcg ataaactgcc gtaattttga tacatctgtg atttaggtca ttaatttaga    5818
taaactagct cattatttcc atctttggaa aagg                                5852

<210> SEQ ID NO 11
<211> LENGTH: 325
<212> TYPE: DNA
<213> ORGANISM: Homo sapiens
<220> FEATURE:

<400> SEQUENCE: 11
ttaaatgctt tacactctgg cgtggaccct aaagaaataa ggttccaaag agccaatctc      60
tcttgataac cctgattatg gttacaagga taccaaacct tccaattcca gatctggaca     120
aagtgtatag ccaatataag acaattatga gaactgccag tgattccaaa tgcagtttcc     180
cactaagtct tttgtatgag atcatcacct gcagtagttg ataagctgaa tagaaagata    240
aggttttcga gaggagaagt gcgccaatgt tgtcttttct ttccacgtta tactgtgtaa    300
ggtgatgttc ccggtcgctg ttgcc                                          325

<210> SEQ ID NO 12
<211> LENGTH: 762
<212> TYPE: DNA
<213> ORGANISM: Homo sapiens
<220> FEATURE:
```

<400> SEQUENCE: 12

```
gatatggaag ttcaaaaggc catgggggat attttgagt cgcttgctgg tgccatttac      60
atgaatagtg ggatgtcact ggagacagtc tggcaggtgt actatcccat gatgcggcca     120
ctaatagaaa agttttctgc aaatgtaccc ggttcccctg tgcgagaatt gcttgaaatg     180
gaaccagaaa ctgccaaatt taggtaagca aaaatgtac atggaaaaaa cattaactta     240
aaaacatcaa aggggaaaag ttcacaaaga tattgtaaac taatgattct gaaaaatatt     300
tacactgtgg tgtgctgttg tcagatttct gtttgtaatc tgattgactt ctctttttc     360
cttctgtttt tatgaaataa tgctgtaata aagactagac ggcagccctg tctgtcgggg     420
gtatgcaatt gcagtaagtc gtaacgcgtg tttcctttgt gtggtgtcag cttatacatg     480
ggactcctgg cctgagagtg cacactaaat gctgattgac aatgataata aatacttctg     540
acttctaatt caagctgttt ggatttttta cagcccggct gagagaactt acgacgggaa     600
ggtcagagtc actgtggaag tagtaggaaa ggggaaattt aaaggtgttg gtcgaagtta     660
caggattgcc aaatctgcag cagcaagaag agccctccga agcctcaaag ctaatcaacc     720
tcaggttccc aatagctgaa accgcttttt aaaattcaaa ac                        762
```

<210> SEQ ID NO 13  
<211> LENGTH: 1607  
<212> TYPE: DNA  
<213> ORGANISM: Homo sapiens  
<220> FEATURE:

<400> SEQUENCE: 13

```
tttaaagcat gccatcacca catatctatt ttgcacttac cctgatgcgc atgagggccg      60
cctttcatat atgagaagca aaaggtcag caactgtaat ctgtatcgcc ttggaaaaaa     120
gaagggacta cccagccgca tggtggtgtc aatatttgat cccctgtga attggcttcc     180
tcctggttat gtagtaaatc aagacaaaag caacacagat aaatgggaaa agatgaaat     240
gacaaaagac tgcatgctgg cgaatggcaa actggatgag gattacgagg aggaggatga     300
ggaggaggag agcctgatgt ggagggctcc gaaggaagag gctgactatg aagatgattt     360
cctggagtat gatcaggaac atatcagatt tatagatagt atgttaatgg ggtcaggagc     420
ttttgtaaag aaaatctctc tttctccttt ttcaaccact gattctgcat atgaatggaa     480
aatgcccaaa aatcctcct taggtagtat gccattttca tcagattttg aggattttga     540
ctacagctct tgggatgcaa tgtgctatct ggatcctagc aaagctgttg aagaagatga     600
ctttgtggtg gggttctgga atccatcaga agaaaactgt ggtgttgaca cgggaaagca     660
gtccatttct tacgacttgc acactgagca gtgtattgct gacaaaagca tagcggactg     720
tgtggaagcc ctgctgggct gctatttaac cagctgtggg gagagggctg ctcagctctt     780
cctctgttca ctggggctga aggtgctccc ggtaattaaa aggactgatc gggaaaaggc     840
cctgtgccct actcgggaga atttcaacag ccaacaaaag aacctttcag tgagctgtgc     900
tgctgcttct gtggccagtt cacgctcttc tgtattgaaa gactcggaat atggttgttt     960
ggagattcca ccaagatgta tgtttgatca tccagatgca gataaaacac tgaatcacct    1020
tatatcgggg tttgaaaatt ttgaaaagaa aatcaactac agattcaaga ataaggctta    1080
ccttctccag gcttttacac atgcctccta ccactacaat actatcactg gtaaggagcc    1140
cacgaccaga cttcatttct gggaaaatga acttttgtgt tgatctcatc gtgttggcct    1200
tgtaaaagtg atctatgcat gtacagtgtt catgcttaat attcaaggga tggggcgggg    1260
```

-continued

```
aacaaaagga atagaaagaa ttcttttcct tgttatttgg ggagcacgta ttgctttata      1320
actttggttg ttgggagtat ggctatcata taccctcatc agtgtcattt tatatctgcc      1380
taattagaga aattttaacc ttagtatttt gatgtgtttt ccccatttta tcctccgcaa      1440
atatctttct cttgcccatt cagtgctgct tttggttttt gatttagttg tatattctgg      1500
atgtatttcc acagccttt attgttcttc ctggacaaaa agaccctcc tttagggtct        1560 ttttaaagat ggatagatta aaagattaaa agcaatgatt tcacaag                    1607
```

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
ctaagttctt tcagagtttc                          20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
aatgtttgag atctctgtgt                          20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
aatcactggc agttctcata                          20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
agggcttttc attcatccag                          20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tctcatacaa aagacttagt                          20

<210> SEQ ID NO 19
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 19
gtctagtctt tattacagca                        20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ccctagatct agatagagac                        20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tcaggccagg agtcccatgt                        20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gtcaatcagc atttagtgtg                        20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
aggtcagttg cagtttcagc                        20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
atagatcact tttacaaggc                        20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ccttaggaaa gtgtctgtaa                        20

```
<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tataaagcaa tacgtgctcc                                                   20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
atgagggtat atgatagcca                                                   20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
ggaaaatttg tctctggctt                                                   20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ggagaaggaa aatttgtctc                                                   20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gtatcttctt tccacaaaaa                                                   20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
caactgctgt gtatcttctt                                                   20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 32
ctatccatct ttaaaaagac                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
attttggtat atcaacaccc                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cttttcaata gctttgtagg                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
taaacggatc acttggtaat                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ataaaatgta ccatcaggca                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
agagttgaat aaaatgtacc                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ggctcgaaga ggtgagttaa                                              20

<210> SEQ ID NO 39
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 39
atattctgca aaagtttcat                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gttttataat attctgcaaa                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
cagtggctgg ttgagattgg                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
acatccagca gtggctggtt                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
tttccccttc tgattcaaat                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
cctcttctca gcactgctta                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
```

-continued ctgcagactt tcccatttgg                                     20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
tggatgtata gcacagagtt                                     20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
ttttctccac agtgatgctg                                     20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
aagttagggt atctaaaatc                                     20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ccgaagtcta agttagggta                                     20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ttttccaccc gaagtctaag                                     20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
tgtgcttaca gtaattatca                                     20

<210> SEQ ID NO 52
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 52
tagcaccttg atgtgcagca                                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
agttcacaga catttggtca                                                    20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gagtccttga ggagtaccca                                                    20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ggccaagagt ccttgaggag                                                    20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
aaaaaggagt cgccaagcat                                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
atgctttaaa aaggagtcgc                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tatgaaaggc ggccctcatg                                                    20
```

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tctcatatat gaaaggcggc                                                 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
gctgaccttt ttgcttctca                                                 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tacagttgct gaccttttg                                                  20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gacaccacca tgcggctggg                                                 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
aggaggaagc caattcacag                                                 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
acataaccag gaggaagcca                                                 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 65
ctttgctagg atccagatag                                                20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
gggagcacct tcagccccag                                                20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
taagccttat tcttgaatct                                                20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
tggtaacaat cagtgatagt                                                20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
ctcccaggaa ttctaagcgc                                                20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
atcgcatctc ccaggaattc                                                20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
agtccaaaat cgcatctccc                                                20

<210> SEQ ID NO 72
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tatgaggtag tccaaaatcg                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
gcttggttat gaggtagtcc                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
taaaggtgct tggttatgag                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ggtcttcata aggtgcttg                                                20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
gagctcagga gagacagctt                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
tttcattctt ctcaagctga                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
```

```
tgcagaaaac ttttctatta                                           20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ttggcagttt ctggttccat                                           20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tatcaaaatt acggcagttt                                           20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
attaatgacc taaatcacag                                           20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
aagcggtttc agctattggg                                           20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
aaactttaaa ttctgccttc                                           20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
atgtcatcat taaagcactc                                           20

<210> SEQ ID NO 85
<211> LENGTH: 20
<212> TYPE: DNA
```

<213> ORGANISM: Artificial Sequence
<220> FEATURE:
<223> OTHER INFORMATION: Antisense Oligonucleotide

<400> SEQUENCE: 85
atctacatca tcctagggac                                                    20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ggcactactg cacacacgga                                                    20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
tcaactactg caggactggc                                                    20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
actatccatg aaggtttcac                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ttagtatgat cctgtaataa                                                    20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
cataaacatt tccatcagtg                                                    20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 91
caatcaatta taaaatctgc                                                                    20
```

ANTISENSE MODULATION OF HELICASE-MOI EXPRESSION

FIELD OF THE INVENTION

The present invention provides compositions and methods for modulating the expression of helicase-moi. In particular, this invention relates to compounds, particularly oligonucleotides, specifically hybridizable with nucleic acids encoding helicase-moi. Such compounds have been shown to modulate the expression of helicase-moi.

BACKGROUND OF THE INVENTION

In addition to functioning as genetic transcripts, RNA molecules play structural and even catalytic roles. Depending on their specific cellular roles, RNA molecules can be largely single stranded or adopt specific tertiary structures. A variety of proteins are necessary to assure the correct folding of RNA molecules and to maintain or modify their specific secondary or tertiary structures. Among these proteins are the RNA helicases of the DEAD-box family and related families (de la Cruz et al., *Trends Biochem. Sci.*, 1999, 24, 192–198). These are involved in various aspects of RNA metabolism, including nuclear transcription, pre-mRNA splicing, ribosome biogenesis, nucleocytoplasmic transport, translation, RNA decay and gene expression. Although generally assumed to be a double-stranded RNA, the substrate might also be an RNA-protein complex. Some investigators therefore refer to these proteins as RNA-dependent NTPases or RNA unwindases, to distinguish them from the processive DNA helicases (de la Cruz et al., *Trends Biochem. Sci.*, 1999, 24, 192–198).

More recently, helicases have been implicated in the process of posttranscriptional gene silencing (PTGS), a form of RNA-mediated interference (Cogoni and Macino, *Science*, 1999, 286, 2342–2344). In this process, the helicase is required to separate the double-stranded DNA before any hybridization and silencing mechanism can be initiated.

The DEAD and DEAH helicase families are closely related helicase groups with their names derived from the sequence of the Walker B motif (DEAD=Asp-Glu-Ala-Asp; DEAH=Asp-Glu-Ala-His) (reviewed in (de la Cruz et al., *Trends Biochem. Sci.*, 1999, 24, 192–198)). The DEXH family is a variation on the DEAH family wherein the third amino acid in the DEAH sequence is variable.

Helicase-moi (also known as KIAA0928, HERNA, delta-K12H4.8 homologue and HEMBA1004199) is a recently discovered helicase gene that encodes a protein belonging to the DEXH-box helicase family (Matsuda et al., *Biochim. Biophys. Acta*, 2000, 1490, 163–169; Nagase et al., *DNA Res.*, 1999, 6, 63–70; Provost et al., *Proc. Natl. Acad. Sci. U. S. A.*, 1999, 96, 1881–1885). In human tissues, helicase-moi is expressed in brain, lung, liver, pancreas and kidney and the gene has been localized to chromosome 14q31 (Matsuda et al., *Biochim. Biophys. Acta*, 2000, 1490, 163–169). Other genes that have been mapped to 14q31 are potential targets involved in Krabble disease, ovarian cancer, and Graves' disease (Matsuda et al., *Biochim. Biophys. Acta*, 2000, 1490, 163–169).

Helicase-moi has been found to interact strongly with the enzyme 5-lipoxygenase which plays a central role in cellular leukotriene synthesis (Provost et al., *Proc. Natl. Acad. Sci. U. S. A.*, 1999, 96, 1881–1885). Since leukotrienes are mediators of inflammation, selective inhibition of potential regulators of leukotriene synthesis, such as helicase-moi, may prove to be an efficient strategy with which to derive treatments for inflammatory disorders. To date, specific inhibitors for helicase-moi have yet to be developed or identified. Consequently, there remains a long felt need for agents capable of effectively and selectively inhibiting the function of helicase-moi.

Antisense technology is emerging as an effective means for reducing the expression of specific gene products and may therefore prove to be uniquely useful in a number of therapeutic, diagnostic, and research applications for the modulation of expression of helicase-moi.

The present invention provides compositions and methods for modulating expression of helicase-moi.

SUMMARY OF THE INVENTION

The present invention is directed to compounds, particularly antisense oligonucleotides, which are targeted to a nucleic acid encoding helicase-moi, and which modulate the expression of helicase-moi. Pharmaceutical and other compositions comprising the compounds of the invention are also provided. Further provided are methods of modulating the expression of helicase-moi in cells or tissues comprising contacting said cells or tissues with one or more of the antisense compounds or compositions of the invention. Further provided are methods of treating an animal, particularly a human, suspected of having or being prone to a disease or condition associated with expression of helicase-moi by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding helicase-moi, ultimately modulating the amount of helicase-moi produced. This is accomplished by providing antisense compounds which specifically hybridize with one or more nucleic acids encoding helicase-moi. As used herein, the terms "target nucleic acid" and "nucleic acid encoding helicase-moi" encompass DNA encoding helicase-moi, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of helicase-moi. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated.

This may be, for example, a cellular gene (or mRNA transcribed from the gene) whose expression is associated with a particular disorder or disease state, or a nucleic acid molecule from an infectious agent. In the present invention, the target is a nucleic acid molecule encoding helicase-moi. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding helicase-moi, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5' UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), known in the art to refer to the portion of an mRNA in the 3' direction from the translation termination codon, and thus including nucleotides between the translation termination codon and 3' end of an mRNA or corresponding nucleotides on the gene. The 5' cap of an MRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U. S. A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such -oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)— —$CH_2$—, —$CH_2$—N($CH_3$)—N ($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$) $_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2NO_2$, $N_3$, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O-$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2' -DMAEOE), i.e., 2—O—$CH_2$—O—$CH_2$—N($CH_2$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—). group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2$—$CH_2$—$CH_2NH_2$), 2'-allyl (2—$CH_2$—CH=$CH_2$), 2'-O-allyl (2'-O-$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3'0 position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base" ) modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3', 2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds.,*Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and United States patent 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluores-ceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of helicase-moi is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding helicase-moi, enabling sandwich and other assays to easily be constructed to exploit this fact. Hybridization of the antisense oligonucleotides of the invention with a nucleic acid encoding helicase-moi can be detected by means known in the art. Such means may include conjugation of an enzyme to the oligonucleotide, radiolabelling of the oligonucleotide or any other suitable detection means. Kits using such detection means for detecting the level of helicase-moi in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082, 624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 $\mu$m in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and etration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p. 92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham MA or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3', 5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NAHCO_3$ and 2×500 mL of saturated NaCl. The organic phase was dried over $Na_2SO_4$. filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'O-methoxyethyl-5'-O-diethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5' -O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2-anhydro-5-methyluridine (149 g, 0.311 mol) and sodium bicarbonate (0.074 g, 0.003 eq) were added with manual stirring. The reactor was sealed and heated in an oil bath until an internal temperature of 160 ° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O -([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirrred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL)

solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.9 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P20. under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-Isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-Dimethylaminoethoxyethoxy (2-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$)$_2$, or 2'-DMAEOE nucleoside amidites) are prepared as follows. Other nucleoside amidites are prepared similarly.

2'-O-[2(2-N,N-dimethylarninoethoxy) ethyl]-5-methyl Uridine

2[2-(Dimethylamino)ethoxy] ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^{2-}$, 2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)-ethyl)]-5-methyl Uridine-3'-O-(cyanoethyl-N,N-diisopropyl)Phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N- dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and Wo 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligo-nucleosides, also identified as amide-4 linked oligonucleo-sides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligo-nucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphor-amidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in IM TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3, H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$p nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACETm MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, MD) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFS were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from th e Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPO-FECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Helicase-moi Expression

Antisense modulation of helicase-moi expression can be assayed in a variety of ways known in the art. For example, helicase-moi mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of helicase-moi can be quantitated in a variety of ways well known in the art, such as immunoprecipitation, Western blot analysis (immunoblotting), ELISA or fluorescence-activated cell sorting (FACS). Antibodies directed to helicase-moi can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+mRNA Isolation

Poly(A)+mRNA was isolated according to Miura et al., *Clin. Chem.*, 1996, 42, 1758–1764. Other methods for poly(A)+mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates we re incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried f or 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells g r own on 100 mm or other standard plates may be treated similarly, using appropriate volumes of all solutions.

Example 12

Total RNA Isolation

Total RNA w as isolated using an RNEASY $_{96}$™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY $_{96}$™ well plate attached to a QIAVAC™ manifold fitted with a waste collection tray and attached to a vacuum source. Vacuum was applied for 15 seconds. 1 mL of Buffer RW1 was added to each well of the RNEASY $_{96}$™ plate and the vacuum again applied for 15 seconds. 1 mL of Buffer RPE was then added to each well of the RNEASY $_{96}$™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13
Real-time Quantitative PCR Analysis of Helicase-moi mRNA Levels

Quantitation of helicase-moi mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRIS™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 $\mu$L PCR cocktail (1× TAQMAN™ buffer A, 5.5 mM $MgCl_2$, 300 $\mu$m each of DATP, dCTP and dGTP, 600 $\mu$M of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 $\mu$L total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, OR). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 $\mu$L of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human helicase-moi were designed to hybridize to a human helicase-moi sequence, using published sequence information (GenBank accession number AB028449, incorporated herein as SEQ ID NO:3). For human helicase-moi the PCR primers were:

forward primer: TTAAAGCATGCCATCACCACAT (SEQ ID NO: 4)

reverse primer: GATTACAGTTGCTGACCTTTTTGC (SEQ ID NO: 5) and the PCR probe was: FAM-ATGCGCATGAGGGCCGCC-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

forward primer: GAAGGTGAAGGTCGGAGTC (SEQ ID NO: 7)

reverse primer: GAAGATGGTGATGGGATTTC (SEQ ID NO: 8) and the

PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of Helicase-moi MRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human helicase-moi, a human helicase-moi specific probe was prepared by PCR using the forward primer TTAAAGCATGCCATCACCACAT (SEQ ID NO: 4) and the reverse primer GATTACAGTTGCTGAC-CTTTTTGC (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human Helicase-moi Expression by Chimeric Phosphorothioate Oligonucleotides Having 2'-NOE Wings and a Deoxy Gap In accordance with the present invention, a series of oligonucleotides were designed to target different regions of the human helicase-moi RNA, using published sequences (GenBank accession number AB028449, incorporated herein as SEQ ID NO: 3, GenBank accession number AB023145, which extends in the 3' direction of GenBank accession number AB028449, incorporated herein as SEQ ID NO: 10, GenBank accession number AA248863, which is an EST variant extending in the 5' direction from position 6396 of GenBank accession number AB028449, the complement of which is incorporated herein as SEQ ID NO: 11, GenBank accession number AW193662, which is an mRNA variant containing an extra 369 nucleotides at position 5790 of GenBank accession number AB028449, the complement of which is incorporated herein as SEQ ID NO: 12, and GenBank accession number AK001827, which extends in the 3, direction of position 5283 of GenBank accession number AB028449, incorporated herein as SEQ ID NO: 13). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human helicase-moi MRNA levels by quantitative real-time PCR as described in other examples herein. Data are averages from two experiments. If present, "N.D." indicates "no data".

TABLE 1

Inhibition of human helicase-moi mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 138602 | 5'UTR | 3 | 2 | ctaagttctttcagagtttc | 69 | 14 |
| 138603 | 5'UTR | 3 | 112 | aatgtttgagatctctgtgt | 46 | 15 |
| 138604 | Exon | 11 | 146 | aatcactggcagttctcata | 11 | 16 |
| 138605 | Start Codon | 3 | 175 | agggcttttcattcatccag | 19 | 17 |
| 138606 | Exon | 11 | 182 | tctcatacaaaagacttagt | 20 | 18 |
| 138607 | Exon | 12 | 381 | gtctagtctttattacagca | 60 | 19 |
| 138608 | Coding | 3 | 427 | ccctagatctagatagagac | 28 | 20 |
| 138609 | Exon | 12 | 476 | tcaggccaggagtcccatgt | 2 | 21 |
| 138610 | Exon | 12 | 501 | gtcaatcagcatttagtgtg | 42 | 22 |
| 138611 | Coding | 3 | 888 | aggtcagttgcagtttcagc | 61 | 23 |
| 138612 | mRNA | 13 | 1197 | atagatcacttttacaaggc | 66 | 24 |
| 138613 | Coding | 3 | 1228 | ccttaggaaagtgtctgtaa | 78 | 25 |
| 138614 | Exon | 13 | 1301 | tataaagcaatacgtgctcc | 53 | 26 |
| 138615 | Exon | 13 | 1340 | atgagggtatatgatagcca | 61 | 27 |
| 138616 | Coding | 3 | 1473 | ggaaaatttgtctctggctt | 70 | 28 |
| 138617 | Coding | 3 | 1479 | ggagaaggaaaatttgtctc | 0 | 29 |
| 138618 | Coding | 3 | 1525 | gtatcttctttccacaaaaa | 62 | 30 |
| 138619 | Coding | 3 | 1535 | caactgctgtgtatcttctt | 74 | 31 |
| 138620 | Exon | 13 | 1557 | ctatccatctttaaaaagac | 0 | 32 |
| 138621 | Coding | 3 | 1760 | attttggtatatcaacaccc | 56 | 33 |
| 138622 | Coding | 3 | 1921 | cttttcaatagctttgtagg | 66 | 34 |
| 138623 | Coding | 3 | 2108 | taaacggatcacttggtaat | 70 | 35 |
| 138624 | Coding | 3 | 2161 | ataaaatgtaccatcaggca | 71 | 36 |
| 138625 | Coding | 3 | 2169 | agagttgaataaaatgtacc | 38 | 37 |
| 138626 | Coding | 3 | 2200 | ggctcgaagaggtgagttaa | 58 | 38 |
| 138627 | Coding | 3 | 3082 | atattctgcaaaagtttcat | 73 | 39 |
| 138628 | Coding | 3 | 3090 | gttttataatattctgcaaa | 49 | 40 |
| 138629 | Coding | 3 | 3130 | cagtggctggttgagattgg | 72 | 41 |
| 138630 | Coding | 3 | 3138 | acatccagcagtggctggtt | 63 | 42 |

TABLE 1-continued

Inhibition of human helicase-moi mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 138631 | Coding | 3 | 3199 | tttcccttctgattcaaat | 36 | 43 |
| 138632 | Coding | 3 | 3229 | cctcttctcagcactgctta | 41 | 44 |
| 138633 | Coding | 3 | 3253 | ctgcagactttcccatttgg | 63 | 45 |
| 138634 | Coding | 3 | 3295 | tggatgtatagcacagagtt | 54 | 46 |
| 138635 | Coding | 3 | 3319 | ttttctccacagtgatgctg | 63 | 47 |
| 138636 | Coding | 3 | 3450 | aagttagggtatctaaaatc | 18 | 48 |
| 138637 | Coding | 3 | 3459 | ccgaagtctaagttagggta | 66 | 49 |
| 138638 | Coding | 3 | 3467 | ttttccacccgaagtctaag | 22 | 50 |
| 138639 | Coding | 3 | 3542 | tgtgcttacagtaattatca | 0 | 51 |
| 138640 | Coding | 3 | 3581 | tagcaccttgatgtgcagca | 23 | 52 |
| 138641 | Coding | 3 | 3626 | agttcacagacatttggtca | 70 | 53 |
| 138642 | Coding | 3 | 4037 | gagtccttgaggagtaccca | 67 | 54 |
| 138643 | Coding | 3 | 4043 | ggccaagagtccttgaggag | 8 | 55 |
| 138644 | Coding | 3 | 4137 | aaaaaggagtcgccaagcat | 13 | 56 |
| 138645 | Coding | 3 | 4144 | atgctttaaaaaggagtcgc | 60 | 57 |
| 138646 | Coding | 3 | 4203 | tatgaaaggcggccctcatg | 39 | 58 |
| 138647 | Coding | 3 | 4210 | tctcatatatgaaaggcggc | 80 | 59 |
| 138648 | Coding | 3 | 4225 | gctgaccttttgcttctca | 92 | 60 |
| 138649 | Coding | 3 | 4232 | tacagttgctgaccttttg | 77 | 61 |
| 138650 | Coding | 3 | 4284 | gacaccaccatgcggctggg | 52 | 62 |
| 138651 | Coding | 3 | 4318 | aggaggaagccaattcacag | 83 | 63 |
| 138652 | Coding | 3 | 4326 | acataaccaggaggaagcca | 72 | 64 |
| 138653 | Coding | 3 | 4718 | ctttgctaggatccagatag | 58 | 65 |
| 138654 | Coding | 3 | 4944 | gggagcaccttcagccccag | 56 | 66 |
| 138655 | Coding | 3 | 5214 | taagccttattcttgaatct | 76 | 67 |
| 138656 | Coding | 3 | 5274 | tggtaacaatcagtgatagt | 57 | 68 |
| 138657 | Coding | 3 | 5294 | ctcccaggaattctaagcgc | 66 | 69 |
| 138158 | Coding | 3 | 5301 | atcgcatctcccaggaattc | 6 | 70 |
| 138659 | Coding | 3 | 5309 | agtccaaaatcgcatctccc | 20 | 71 |
| 138660 | Coding | 3 | 5317 | tatgaggtagtccaaaatcg | 32 | 72 |
| 138661 | Coding | 3 | 5324 | gcttggttatgaggtagtcc | 22 | 73 |
| 138662 | Coding | 3 | 5331 | taaaggtgcttggttatgag | 15 | 74 |
| 138663 | Coding | 3 | 5339 | ggtcttcataaaggtgcttg | 8 | 75 |
| 138664 | Coding | 3 | 5464 | gagctcaggagagacagctt | 53 | 76 |
| 138665 | Coding | 3 | 5513 | tttcattcttctcaagctga | 21 | 77 |
| 138666 | Coding | 3 | 5710 | tgcagaaaactttctatta | 80 | 78 |
| 138667 | Coding | 3 | 5766 | ttggcagtttctggttccat | 70 | 79 |
| 138668 | 3'UTR | 10 | 5771 | tatcaaaattacggcagttt | 76 | 80 |
| 138669 | 3'UTR | 10 | 5794 | attaatgacctaaatcacag | 59 | 81 |
| 138670 | Stop Codon | 3 | 5946 | aagcggtttcagctattggg | 46 | 82 |
| 138671 | 3'UTR | 3 | 6064 | aaactttaaattctgccttc | 60 | 83 |
| 138672 | 3'UTR | 3 | 6218 | atgtcatcattaaagcactc | 72 | 84 |
| 138673 | 3'UTR | 3 | 6340 | atctacatcatcctagggac | 75 | 85 |
| 138674 | 3'UTR | 3 | 6373 | ggcactactgcacacacgga | 16 | 86 |
| 138675 | 3'UTR | 3 | 6390 | tcaactactgcaggactggc | 75 | 87 |
| 138676 | 3'UTR | 3 | 6626 | actatccatgaaggtttcac | 60 | 88 |
| 138677 | 3'UTR | 3 | 6755 | ttagtatgatcctgtaataa | 20 | 89 |
| 138678 | 3'UTR | 3 | 6904 | cataaacatttccatcagtg | 85 | 90 |
| 138679 | 3'UTR | 3 | 6996 | caatcaattataaaatctgc | 32 | 91 |

As shown in Table 1, SEQ ID NOs 14, 15, 19, 22, 23, 24, 25, 26, 27, 28, 30, 31, 33, 34, 35, 36, 37, 38, 39, 40, 41, 42, 43, 44, 45, 46, 47, 49, 53, 54, 57, 58, 59, 60, 61, 62, 63, 64, 65, 66, 67, 68, 69, 72, 76, 78, 79, 80, 81, 82, 83, 84, 85, 87, 88, 90 and 91 demonstrated at least 30% inhibition of human helicase-moi expression in this assay and are therefore preferred. The target sites to which these preferred sequences are complementary are herein referred to as "active sites" and are therefore preferred sites for targeting by compounds of the present invention.

Example 16

Western Blot Analysis of Helicase-moi Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to helicase-moi is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 16 to 50 nucleobases in length targeted to nucleobases 427 through 5785 of a coding region of a nucleic acid molecule encoding human helicase-moi of SEQ ID NO:3, wherein said compound specifically hybridizes with said region and inhibits the expression of human helicase-moi.

2. The compound of claim 1 which is an antisense oligonucleotide.

3. A compound up to 50 nucleobases in length comprising at least a 16-nucleobase portion of SEQ ID NO: 14, 15, 19, 22, 23, 24, 25, 26, 27, 28, 30, 31, 33, 34, 35, 36, 37, 38, 39, 40, 41, 42, 43, 44, 45, 46, 47, 49, 53, 54, 57, 58, 59, 60, 61, 62, 63, 64, 65, 66, 67, 68, 69, 72, 76, 78, 79, 80, 81, 82, 83, 84, 85, 87, 88, 90 or 91 which inhibits the expression of human helicase-moi.

4. The compound of claim 2 wherein the antisense oligonucleotide comprises at least one modified internucleoside linkage.

5. The compound of claim 4 wherein the modified internucleoside linkage is a phosphorothioate linkage.

6. The compound of claim 2 wherein the antisense oligonucleotide comprises at least one modified sugar moiety.

7. The compound of claim 6 wherein the modified sugar moiety is a 2'-O-methoxyethyl sugar moiety.

8. The compound of claim 2 wherein the antisense oligonucleotide comprises at least one modified nucleobase.

9. The compound of claim 8 wherein the modified nucleobase is a 5-methylcytosine.

10. The compound of claim 2 wherein the antisense oligonucleotide is a chimeric oligonucleotide.

11. A composition comprising the compound of claim 1 and a pharmaceutically acceptable carrier or diluent.

12. The composition of claim 11 further comprising a colloidal dispersion system.

13. The composition of claim 11 wherein the compound is antisense oligonucleotide.

14. A method of inhibiting the expression of human helicase-moi in cells or tissues comprising contacting said cells or tissues in vitro with the compound of claim 1 so that expression of human helicase-moi is inhibited.

15. The compound of claim 3 which is an antisense oligonucleotide.

16. The compound of claim 15 wherein the antisense oligonucleotide comprises at least one modified internucleoside linkage.

17. The compound of claim 16 wherein the modified internucleoside linkage is a phosphorothioate linkage.

18. The compound of claim 15 wherein the antisense oligonucleotide comprises at least one modified sugar moiety.

19. The compound of claim 18 wherein the modified sugar moiety is a 2'-O-methoxyethyl sugar moiety.

20. The compound of claim 15 wherein the antisense oligonucleotide comprises at least one modified nucleobase.

21. The compound of claim 20 wherein the modified nucleobase is a 5-methylcytosine.

22. The compound of claim 15 wherein the antisense oligonucleotide is a chimeric oligonucleotide.

23. A composition comprising the compound of claim 3 and a pharmaceutically acceptable carrier or diluent.

24. The composition of claim 23 further comprising a colloidal dispersion system.

25. The composition of claim 23 wherein the compound is an antisense oligonucleotide.

26. A method of inhibiting the expression of human helicase-moi in cells or tissues comprising contacting said cells or tissues in vitro with the compound of claim 3 so that expression of human helicase-moi is inhibited.

* * * * *